July 18, 1967 W. E. LAMMERTS Plant Pat. 2,755
ROSE PLANT
Filed June 20, 1966
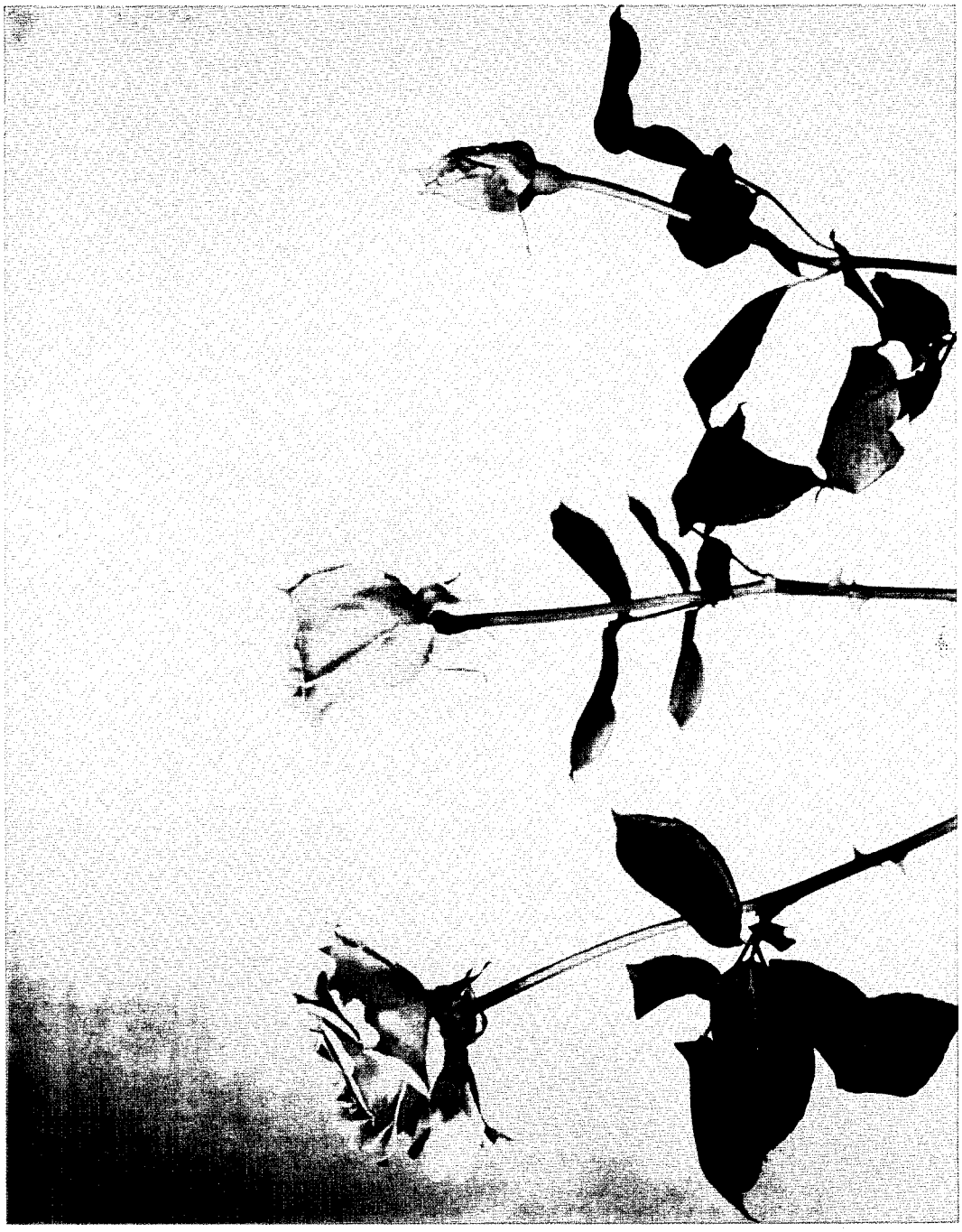
Inventor.
Walter E. Lammerts
By: Robb & Robb
Attorneys.

United States Patent Office

Plant Pat. 2,755
Patented July 18, 1967

2,755
ROSE PLANT

Walter E. Lammerts, Freedom, Calif., assignor to Amling-De Vor Nurseries, Inc., Livermore, Calif., a corporation of California Filed June 20, 1966, Ser. No. 559,007
1 Claim. (Cl. Plt.—18)

The present invention relates to a new and distinct variety of rose plant of the hybrid tea class, which was originated be me by crossing the rose variety known as "Queen Elizabeth" (Plant Patent No. 1,259) with the variety known as "Tawny Gold" (Plant Patent No. 950), the former being the seed parent and the latter being the pollen parent.

As the result of this breeding, I have produced a new and improved rose variety which is distinctly different from its parents, as well as from all other rose varieties, as evidenced by the following unique combination of characteristics which are outstanding therein:

(1) A vigorous and upright habit of growth, with a typical hybrid tea branching habit;

(2) Attractive, glossy and mildew-resistant foliage which clothes the plant well;

(3) Long, urn-shaped buds;

(4) Production of large, high-centered and regularly imbricated open blooms of excellent form and firm substance and borne singly on long and strong stems;

(5) A distinctive and attractive Neyron Rose general color tonality of the blooms, and which is very stable and uniform;

(6) Long-lasting qualities of the blooms, both on the bush and as cut flowers, particularly in the ⅓ to ¾ open stage; and (7) A moderate tea fragrance of the blooms.

In comparison with its seed parent, "Queen Elizabeth," the canes of the new variety are less stiffly upright, and the branching habit is more typical of the hybrid tea type than is the case of this parent.

The new variety bears some resemblance in general habit, bloom habit and bloom color to the rose varieties "Capistrano" (Plant Patent No. 922) and "Tiffany" (Plant Patent No. 1,304), but "Capistrano" differs particularly from the new variety by its more penetrating flower fragrance, less recurving of the flower petals, shorter bloom life, much less bloom production, and stiffer and less graceful general habit, while "Tiffany" has a more upright habit than the new variety, fatter buds, the presence of petaloids, a more marked flower fragrance, a less even and less stable bloom color, and a much lighter color on the reverse of the flower petals.

Asexual reproduction of my new variety by budding, as performed by me at Livermore, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the British Colour Council, except where general color terms of ordinary dictionary significance are obvious, as based upon observations of specimens grown at West Los Angeles, Calif.:

Type: Half-hardy; greenhouse and outdoor; seedling; for cut flowers and for garden decoration.

Class: Hybrid tea.

Breeding: Seedling.

*Seed parent.*—"Queen Elizabeth."

*Pollen parent.*—"Tawny Gold."

Propagation: Holds its distinguishing characteristics through succeeding propagations by budding.

*Flower*

Flowers borne: Singly; on long, strong stems.

Quantity of bloom: Free, both outdoors and in greenhouses.

Continuity: Continuous.

Fragrance: Moderate. Nature—tea.

Bud:

*Peduncle.*—Long; erect; stiff; entirely smooth. Color—medium green.

*Before calyx breaks.*—Size—medium. Form—pointed; with a conspicuous neck; with occasional foliaceous appendages on the surface of the bud; with foliaceous parts extending beyond the tip of the bud equal to ¼ to ½ or more of its length. Color—Pea Green, Plate 61.

*As calyx breaks.*—Color—Scheele's Green, Plate 860/3.

*As first petal opens.*—Size—large. Form—globular. Color: outside—Neyron Rose, Plate 623/3; inside—Neyron Rose, Plate 623/1.

*Openings.*—Opens up well.

Bloom:

*Size (when fully open).*—Large; from 5 inches to 6 inches.

*Petalage.*—Very double; from 30 to 35 petals; arranged regularly.

*Form.*—High-centered at first and remaining high-centered; petals being at first rolled outward and later becoming loosely rolled outward at maturity.

Petals:

*Texture.*—Thick.

*Appearance.*—Inside—velvety. Outside—satiny.

*Shape.*—Outside—round; scalloped; with apex flat. Intermediate—from round to ovate, with slightly pointed center. Inside—round, with slightly pointed center.

This description of a newly opened flower was made from a rose grown in a greenhouse in the month of March at West Los Angeles, Calif.:

*Color.*—Outer petal: outside surface—Neyron Rose, Plate 623/1; inside surface—Neyron Rose, Plate 623/1. Intermediate petal: outside surface—Neyron Rose, Plate 623/1; inside surface—Neyron Rose, Plate 623/1. Inner petal: outside surface—Neyron Rose, Plate 623/1; inside surface—Neyron Rose, Plate 623/1.

This description was made from a rose that was open for three days in a greenhouse in the month of March at West Los Angeles, Calif.:

*Color.*—Outer petal: outside surface—Neyron Rose, Plate 623/2; inside surface—Neyron Rose, Plate 623/2. Inner petal: outside surface—Neyron Rose, Plate 623/1; inside surface—Neyron Rose, Plate 623/1.

*General color effect.*—Newly opened flower—Neyron Rose, Plate 623/1. 3-days open—Neyron Rose, Plate 623/1.

*Behavoir.*—Drop off cleanly.

*Flower longevity.*—On bush in garden—5 days in August. Cut roses grown outdoors and kept at living-room temperatures—5 days in August. Cut roses grown in greenhouse and kept at living-room temperatures—6 days in March.

*Reproductive organs*

Stamens: Many; arranged regularly about pistils.
Filaments: Medium length; with anthers. Color—yellow.
Anthers: Medium size; open at various times. Color—yellow.
Pollen: Moderate quantity. Color—gold.
Pistils: Medium number.
Styles: Uneven; medium length; thin; bunched.
Stigma: Color—yellow with red.
Ovaries: All enclosed in calyx.
Hips: None.
Sepals: Falling soon; spear-shaped; recurved. Color—Agathia Green, Plate 60/1.
Seeds: None.

*Plant*

Foliage:

*Leaves.*—Compound of 5 leaflets; abundant; medium large size; heavy; glossy.

*Leaflets.*—Shape—ovoid. Apex—acute. Base—round. Margin—serrate.

*Color.*—Mature: upper surface—dark green; under surface—light green. Young: upper surface—light green; under surface—green-bronze.

*Rachis (the supporting stem of the compound leaf).*—Medium caliper. Upper side—grooved; slightly rough. Under side—smooth; occasionally one thorn.

*Stipules.*—Narrow; with medium length points turning out at an angle of less than 45°; recurved toward the stem.

*Disease resistance.*—Good resistance to mildew, as determined by comparison with other varieties grown under comparable cultural conditions at Shafter, Calif.

Growth:

*Habit.*—Upright.

*Growth.*—Vigorous.

*Canes.*—Medium caliper.

*Main stems.*—Color — green. Thorns — medium length; straight; with narrow base. Prickles—none. Hairs—none.

*Branches.*—Color—bright green. Thorns—several; medium length; straight; with narrow base. Prickles—none. Hairs—none.

*New shoots.*—Color—bright green. Thorns—several; medium length; straight; with narrow base. Prickles—none. Hairs—none.

I claim:

A new and distinct variety of rose plant of the hybrid tea class, substantially as herein shown and described, characterized particularly as to novelty by the unique combination of a vigorous and upright habit of growth, with a typical hybrid tea branching habit; attractive, glossy and mildew-resistant foliage which clothes the plant well; long, urn-shaped buds; production of large, high-centered and regularly imbricated open blooms of excellent form and firm substance and borne singly on long and strong stems; a distinctive and attractive Neyron Rose general color tonality of the blooms and which is very stable and uniform; long-lasting qualities of the blooms, both on the bush and as cut flowers, particularly in the ⅓ to ¾ open stage, and a moderate tea fragrance of the blooms.

No references cited.

ABRAHAM G. STONE, *Primary Examiner.*

ROBERT E. BAGWILL, *Examiner.*